United States Patent
Sawhney

(10) Patent No.: US 7,780,980 B2
(45) Date of Patent: *Aug. 24, 2010

(54) METHODS OF USING IN SITU HYDRATION OF HYDROGEL ARTICLES FOR SEALING OR AUGMENTATION OF TISSUE OR VESSELS

(75) Inventor: Amarpreet S. Sawhney, Bedford, MA (US)

(73) Assignee: Incept, LLC, Bedford, MA (US)

( * ) Notice: Subject to any disclaimer, the term of this patent is extended or adjusted under 35 U.S.C. 154(b) by 728 days.

This patent is subject to a terminal disclaimer.

(21) Appl. No.: 11/406,791

(22) Filed: Apr. 19, 2006

(65) Prior Publication Data

US 2006/0193899 A1  Aug. 31, 2006

Related U.S. Application Data

(63) Continuation of application No. 10/616,055, filed on Jul. 9, 2003, which is a continuation of application No. 09/134,199, filed on Aug. 14, 1998, now Pat. No. 6,605,294.

(51) Int. Cl.
| | |
|---|---|
| *A61K 9/70* | (2006.01) |
| *A61B 17/03* | (2006.01) |
| *A61F 2/00* | (2006.01) |
| *A61F 2/82* | (2006.01) |
| *A61F 13/00* | (2006.01) |
| *A61K 47/30* | (2006.01) |
| *A61L 31/04* | (2006.01) |

(52) U.S. Cl. ............... 424/443; 128/887; 424/422; 424/423; 424/426; 424/444; 424/486; 514/772.3; 606/213; 623/1.1; 623/1.38

(58) Field of Classification Search ............ None
See application file for complete search history.

(56) References Cited

U.S. PATENT DOCUMENTS

| | | | |
|---|---|---|---|
| 3,640,741 A | 2/1972 | Etes | |
| 3,865,105 A | 2/1975 | Lode | |
| 3,865,108 A | 2/1975 | Hartop | |
| 3,975,350 A | 8/1976 | Hudgin et al. | |
| 3,991,766 A | 11/1976 | Schmitt et al. | |
| 3,992,562 A | 11/1976 | Denzinger et al. | |
| 4,001,391 A | 1/1977 | Feinstone et al. | |
| 4,002,173 A | 1/1977 | Manning et al. | |
| 4,014,335 A | 3/1977 | Arnold | |
| 4,207,893 A | 6/1980 | Michaels | |
| 4,327,709 A | 5/1982 | Hanson et al. | |
| 4,351,922 A | 9/1982 | Yoshida et al. | |
| 4,369,229 A | 1/1983 | Shah | |
| 4,509,504 A | 4/1985 | Brudin | |
| 4,655,211 A | 4/1987 | Sakamoto et al. | |
| 4,741,872 A | 5/1988 | Deluca et al. | |
| 4,826,945 A | 5/1989 | Cohn et al. | |
| 4,852,568 A | 8/1989 | Kensey | |
| 4,890,612 A | 1/1990 | Kensey | |
| 4,938,763 A | 7/1990 | Dunn et al. | |
| 4,948,575 A | 8/1990 | Cole et al. | |
| 5,090,955 A | 2/1992 | Simon | |
| 5,090,995 A | 2/1992 | Kubota et al. | |
| 5,100,992 A | 3/1992 | Cohn et al. | |
| 5,104,909 A | 4/1992 | Grasel et al. | |
| 5,160,745 A | 11/1992 | Deluca et al. | |
| 5,171,148 A | 12/1992 | Wasserman et al. | |
| 5,198,220 A | 3/1993 | Damani | |
| 5,258,042 A | 11/1993 | Mehta | |
| 5,290,310 A | 3/1994 | Makower et al. | |
| 5,324,775 A | 6/1994 | Rhee et al. | |
| 5,341,993 A | 8/1994 | Haber et al. | |
| 5,368,563 A | 11/1994 | Lonneman et al. | |
| 5,383,896 A | 1/1995 | Gershony et al. | |
| RE34,866 E | 2/1995 | Kensey et al. | |
| 5,391,183 A | 2/1995 | Janzen et al. | |
| 5,410,016 A | 4/1995 | Hubbell et al. | |
| 5,413,571 A | 5/1995 | Katsaros et al. | |
| 5,423,821 A | 6/1995 | Pasque | |
| 5,431,639 A | 7/1995 | Shaw | |
| 5,437,292 A | 8/1995 | Kipshidze et al. | |
| 5,441,517 A | 8/1995 | Kensey et al. | |
| 5,456,693 A | 10/1995 | Conston et al. | |
| 5,510,418 A | 4/1996 | Rhee et al. | |

(Continued)

FOREIGN PATENT DOCUMENTS

WO    WO 00/19912    4/2000

OTHER PUBLICATIONS

U.S. Appl. No. 11/465,791, filed Oct. 2007, Sawhney et al.*

(Continued)

*Primary Examiner*—Yvonne L Eyler
*Assistant Examiner*—Christopher R Lea
(74) *Attorney, Agent, or Firm*—Dardi & Herbert, PLLC

(57) ABSTRACT

Pharmaceutically acceptable hydrogel polymers of natural, recombinant or synthetic origin, or hybrids thereof, are introduced in a dry, less hydrated, or substantially deswollen state and rehydrate in a physiological environment to undergo a volumetric expansion and to affect sealing, plugging, or augmentation of tissue, defects in tissue, or of organs. The hydrogel polymers may deliver therapeutic entities by controlled release at the site. Methods to form useful devices from such polymers, and to implant the devices are provided.

14 Claims, No Drawings

U.S. PATENT DOCUMENTS

| | | | |
|---|---|---|---|
| 5,514,379 | A | 5/1996 | Weissleder et al. |
| 5,522,898 | A | 6/1996 | Bao |
| 5,529,914 | A | 6/1996 | Hubbell et al. |
| 5,580,923 | A | 12/1996 | Yeung et al. |
| 5,605,541 | A | 2/1997 | Holm |
| 5,624,685 | A | 4/1997 | Takahashi et al. |
| 5,645,583 | A | 7/1997 | Villain et al. |
| 5,668,236 | A | 9/1997 | Engelhardt et al. |
| 5,688,855 | A | 11/1997 | Stoy et al. |
| 5,698,213 | A | 12/1997 | Jamiolkowski et al. |
| 5,714,159 | A | 2/1998 | Shalaby |
| 5,752,974 | A | 5/1998 | Rhee et al. |
| 5,786,439 | A | 7/1998 | Van Antwerp et al. |
| 5,820,918 | A | 10/1998 | Ronan et al. |
| 5,826,584 | A | 10/1998 | Schmitt |
| 5,843,743 | A | 12/1998 | Hubbell et al. |
| 5,849,412 | A | 12/1998 | Bromberg et al. |
| 5,874,500 | A | 2/1999 | Rhee et al. |
| 6,051,248 | A | 4/2000 | Sawhney et al. |
| 6,063,061 | A * | 5/2000 | Wallace et al. ............. 604/181 |
| 6,100,346 | A | 8/2000 | Jamiolkowski et al. |
| 6,133,325 | A | 10/2000 | Schwartz et al. |
| 6,162,241 | A | 12/2000 | Coury et al. |
| 6,166,130 | A | 12/2000 | Rhee et al. |
| 6,258,351 | B1 | 7/2001 | Harris |
| 6,271,278 | B1 * | 8/2001 | Park et al. .................. 521/150 |
| 6,458,147 | B1 | 10/2002 | Cruise et al. |
| 6,605,294 | B2 * | 8/2003 | Sawhney ................... 424/426 |
| 6,613,070 | B2 | 9/2003 | Redmond et al. |
| 6,699,261 | B1 | 3/2004 | Cates et al. |
| 7,001,410 | B2 | 2/2006 | Fisher et al. |

OTHER PUBLICATIONS

Onishi et al., "Study of Dextran-Methyl Methacrylate Graft Copolymer," Contemporary Topics in Polymer Science, Bailey, W.J. eds., Plenum Press, New York, 4:149-162 (1984).

Park et al., Biodegradable Hydrogels for Drug Delivery, Technomic Publishing Co., Inc. Lancaster, Pennsylvania (1993).

Office Actions and Amendments of U.S. Appl. No. 10/616,055, (2008).

Abusafieh, A. et al., "Development of Self-Anchoring Bone Implants. I. Processing and Material Characterization," J. Biomat. Mater. Res., (Appi. Biomater.), 38:314-327 (1997).

Bhatia, S. et al., "The Effect of Site of Implantation and Animal Age on Properties of Polydioxanone Pins," J. Biomater. *Sci., Polymer. Edn.*, Bamford, C.H. et al., eds., 6(5): 435-446 (1994).

Brundin, J., "Hydrogel Tubal Blocking Device: P-Block," Female Transcervical Sterilization, Zatuchni, G.I. et aI., eds., Harper & Row, Philadelphia, Pennsylvania, 240-244 (1982).

Chisholm, et al., "Fibrin Sealant as a Plug for the Post Liver Biopsy Needle Track," Clinical Radiology, 40(6):627-628 (1989).

Greenberg, et al., "Stimulation of Bone Formation by a Swelling Endosseous Implant," J.Biomed. Maters. Research, 12:929-933 (1978).

Handbook of Common Polymers, compiled by Roff, W.J. et aI., CRC Press, Cleveland, Ohio, (1972).

Jarrett et al., "Bioabsorbable Hydrogel Tissue Barrier: In Situ Gelation Kinetics," Soc. for Biomater., Transactions of 21 st Annual Meeting: 182 (1995).

Medicinal Chemistry, 3rd Ed., Parts 1 and 2, Burger, A., ed., Wiley-Interscience, (1970).

Nagaoka et al., "Interaction Between Blood Components and Hydrogels with Poly(oxyethylene) Chains," Polymers As Biomaterials, Shalaby, S.W. et al., eds., Plenum Press, New York, 361-374 (1984).

Okano, et al., "Effect of Hydrophilic and Hydrophobic Microdomains on Mode of Interaction Between Block Polymer and Blood Platelets," J. Biomed. Mats. Research. 15:393-402 (1981).

Park, "Enzyme-Digestible Swelling Hydrogels as Platforms for Long-Term Oral Drug Delivery: Synthesis and Characterization," Biomaterials, 9:435-441 (1988).

Remington's Pharmaceutical Sciences, 14th Ed., I.E. Hoover et aI., eds., Mack Publishing Co., Easton, Pennsylvania (1970).

Sawhney, et al., "Bioerodible Hydrogels Based on Photopolymerized Poly(ethylene glycol)-co-poly(a-hydroxy acid) Diacrylate Macromers," Macromolecules, 26:581-587 (1993).

Shah, "Hydrophilic-Hydrophobic Domain Polymer Systems," Water Soluble Polymers, Chap. 30, Shalaby, S.W. et al., eds., Amer. Chern. Soc., Washington, D.C., 467-483 (1991).

Shah, "Novel Two-Phase Polymer System," Polymer, 28:1212-1216 (1987).

Shalaby, "Bioabsotbable Polymers," Encyclopedia of Pharmaceutical Technology, Swarbrick, I. et aI., eds., Marcel Dekker, Inc., New York, 1 :465-476 (1988).

The Drug. The Nurse. The Patient (Including Current Drug Handbook), Falconer's 7th Ed., W.B. Saunders Co., Philadelphia, Pennsylvania (1974).

* cited by examiner

METHODS OF USING IN SITU HYDRATION OF HYDROGEL ARTICLES FOR SEALING OR AUGMENTATION OF TISSUE OR VESSELS

CROSS-REFERENCE TO RELATED APPLICATIONS

This application is a continuation of application Ser. No. 10/616,055 filed Jul. 9, 2003, which in turn is a continuation application Ser. No. 09/134,199, filed Aug. 14, 1998, now U.S. Pat. No. 6,605,294, issued Aug. 12, 2003, which are hereby incorporated by reference

FIELD OF THE INVENTION

This invention relates to making and using medically useful articles formed from hydrogels. More specifically, the present invention relates to the methods of using in situ hydration of hydrogel articles to seal or augment tissues or organs.

BACKGROUND OF THE INVENTION

Hydrogels are materials that absorb solvents (such as water), undergo rapid swelling without discernible dissolution, and maintain three-dimensional networks capable of reversible deformation. See, e.g., Park, et al., *Biodegradable Hydrogels for Drug Delivery*, Technomic Pub. Co., Lancaster, Pa. (1993).

Hydrogels may be uncrosslinked or crosslinked. Uncrosslinked hydrogels are able to absorb water but do not dissolve due to the presence of hydrophobic and hydrophilic regions. A number of investigators have explored the concept of combining hydrophilic and hydrophobic polymeric components in block (Okano, et al., "Effect of hydrophilic and hydrophobic microdomains on mode of interaction between block polymer and blood platelets", *J. Biomed. Mat. Research,* 15:393-402 (1981), or graft copolymeric structures (Onishi, et al., in *Contemporary Topics in Polymer Science*, (Bailey & Tsuruta, Eds.), Plenum Pub. Co., New York, 1984, p. 149), and blends (Shah, "Novel two-phase polymer system," *Polymer,* 28:1212-1216 (1987) and U.S. Pat. No. 4,369,229 to Shah) to form the "hydrophobic-hydrophilic" domain systems, which are suited for thermoplastic processing. See, Shah, Chap. 30, in *Water Soluble Polymers* (Shalaby et al., Eds.), Vol. 467, ACS-Symp. Ser., Amer. Chem. Soc., Washington (1991). These uncrosslinked materials can form hydrogels when placed in an aqueous environment.

Hydrogels may be formed by physical or chemical crosslinking, or a combination of these two processes. Physical crosslinking takes place as a result of ionic linkages, hydrogen bonding, Van der Waals forces, or other such physical forces. Chemical crosslinking occurs due to the formation of covalent linkages. Covalently crosslinked networks of hydrophilic polymers, including water-soluble polymers are traditionally denoted as hydrogels (or aquagels) in the hydrated state. Hydrogels have been prepared based on crosslinked polymeric chains of methoxypoly(ethylene glycol) monomethacrylate having variable lengths of the polyoxyethylene side chains, and their interaction with blood components has been studied (Nagaoka et al., in *Polymers as Biomaterial* (Shalaby et al., Eds.) Plenum Press, 1983, p. 381). A number of aqueous hydrogels have been used in various biomedical applications, such as, for example, soft contact lenses, wound management, and drug delivery.

The concept of injecting hydrogels to fill spaces or tracks is described in U.S. Pat. No. 5,645,583 to Villain et al. That patent describes a polyethylene oxide gel implant that may be injected into a human body for tissue replacement and augmentation. U.S. Pat. No. 5,090,955 to Simon describes the use of gels in ophthalmology for corneal tissue augmentation procedures such as Gel Injection Adjustable Keratoplasty (GIAK). Neither patent mentions of augmentation of such tissue by hydration and swelling-induced shape changes in the tissue. Instead, for example, the Simon patent describes "smoothing and massaging" of the cornea to remove excess hydrogel material.

Non-degradable hydrogels made from poly(vinyl pyrrolidone) and methacrylate have been fashioned into fallopian tubal occluding devices that swell and occlude the lumen of the tube. See, Brundin, "Hydrogel tubal blocking device: P-Block", in *Female Transcervical Sterilization*, (Zatuchini et al., Eds.) Harper Row, Philadelphia (1982), pp. 240-244. Because such hydrogels undergo a relatively small amount of swelling and are not absorbable, so that the sterilization is not reversible, the devices described in the foregoing reference have found limited utility.

U.S. Pat. No. 5,324,775 to Rhee et al. describes injectable particles based on swellable natural polymers that may be suspended in a non-aqueous fluid, e.g., an oil. The particles are formed from ground solid articles and may be injected into soft tissue to rehydrate in-situ to augment the tissue. A significant drawback of the compositions described in that patent, however, is the requirement that a non-aqueous and water insoluble carrier be used to inject the particles.

In view of the foregoing, it would be desirable to provide methods of using hydrogel materials, for example, for temporary occlusion of a body lumen or for tissue augmentation, that overcome the drawbacks of previously known compositions and methods.

It therefore would be desirable to provide methods of forming and using medically useful articles that comprise absorbable hydrogels, capable of undergoing a relatively large degree of swelling in-situ.

In addition to tissue augmentation and lumen occlusion, absorbable hydrogel articles may have application in sealing surgically created voids. For example, tissue biopsy is a very commonly performed minor surgical procedure, and is often to confirm or rule out the presence of disease that has been identified by a previously undertaken diagnostic modality, e.g., X-rays or ultrasound imaging.

Often needle biopsies are performed on solid organs using needles that are introduced from the outside of the patient's body, across the pelvic or thoracic wall. Visualization in performing such procedures is typically limited and the cutting action of the needle often generates associated complications subsequent to the biopsy. Increasing experience with percutaneous biopsy has clarified some subtle points and controversies about possible complications and their prevention.

For example, while hemorrhage is possible with even the smallest aspiration needle, the risk has generally been assumed to increase significantly with the use of larger cutting needles and/or in patients with coagulation deficiencies. Some argue that the benefits attained with the use of cutting needles therefore is not worth the added risk. Unfortunately, while fine-needle aspiration techniques may provide the necessary tissue for cytologic diagnosis in many cases, there are situations in which cutting needles are needed for optimal diagnostic accuracy, such as biopsy of the retroperitoneum (when lymphoma is likely and must be typed) and in the diagnosis of unusual neoplasms, benign neoplasms, or diffuse hepatic or renal parenchymal diseases.

Even though needle biopsy is widely regarded as safe, often times leaks may develop in the underlying tissues due to the needle puncture. For example, when conducting a needle biopsy of the lung, air leaks may develop, leading to collapse of the lung and/or pneumothorax. The incidence of clinically significant pneumothorax following needle biopsy has been reported to be in the 15-25% range. Needle biopsy also is used to assess whether kidney transplantation has been successful, and is associated with the formation of arteriovenous fistulae in 10-15% of cases. Likewise, biopsy of the liver and spleen lead to bleeding complications in 5-10% of cases.

Liver biopsy is essential to the management of liver diseases. Although generally safe, the presence of a vascular tumor, bleeding diathesis or ascites makes the procedure more hazardous. The development of transvenous hepatic biopsy techniques have been one response to this problem. Prevention of hemorrhagic complications in high-risk patients has been accomplished with different clinical methods, and with varying degrees of success. Several authors have suggested use of a transjugular route for biopsy of the liver in high-risk patients. More recently, others have suggested that cutting needles may be used in conjunction with various methods to plug the needle track, for example, with steel embolization coils or gelatin sponge particles, such as GELFOAM®, manufactured by Upjohn, Inc., Kalamazoo, Mich.

U.S. Pat. No. 5,522,898 to Bao describes a closure device for the repair of skin tissue, controlling bleeding, and reducing the likelihood of inducing excess scar tissue during a routine skin biopsy procedure, using a cylindrical tube made from a foam material which is absorbed in a biopsy site with little tissue reaction. That patent also describes the use of GELFOAM® for topical applications. While GELFOAM® may be effective in preventing bleeding, the sponge has a particulate structure, and is difficult to inject smoothly down a needle track. The risk of clumping and the subsequent scarcity of sponge along the needle track presents a risk of bleeding after non-uniform embolization.

Chisholm et al., in "Fibrin Sealant as a Plug for the Post Liver Biopsy Needle Track," *Clinical Radiology*, 40:627-628 (1989) propose the use of fibrin sealants to embolize a needle track. A drawback of this technique, however, is that fibrin sealants are associated with a theoretical risk of disease transmission due to the human and animal proteins that are the constituents of fibrin sealants.

Needle biopsies of other parenchymal tissues, such as kidney or lung tissue, also often result in prolonged hemorrhage or airleak from the site of the biopsy. This especially may present a problem when multiple biopsies are to be obtained from a particular organ.

It therefore would be desirable to provide hydrogel articles and methods for plugging voids created in tissue during surgical procedures, such as a needle track created during a biopsy, so as to reduce the risk of hemorrhage after tissue removal.

Abusafieh et al., in "Development of Self-Anchoring Bone Implants. I. Processing and Material Characterization," *J. Biomed Mater Res.*, 38:314-327 (1997) describe the development of a self anchoring bone implant formed by polymerizing hydrogels around carbon and KEVLAR® fibers, a registered trademark of E.I. DuPont de Nemours, Inc., Wilmington, Del. The concept of self-anchoring swelling-type orthopedic implants is described by Greenberg et al. in "Stimulation of Bone Formation by a Swelling Endosseous Implant," *J. Biomed Mater Res.*, 12:922-933 (1978). Such implants would, in principle, dilate in a controlled manner by absorption of body fluids to achieve fixation by an expansion-fit mechanism.

Although research on swelling-type bone implants began more than 15 years ago, exploitation of this concept has been largely hampered by the inability to produce a material with the desired hydromechanical properties. None of the previously known materials are made from absorbable hydrogels and all are essentially permanent implants. Also, because there is a degradation in mechanical properties that accompanies swelling, hydration for such materials has been restricted to less than 5-8% by weight and takes place over long periods of time (several days). Since these previous known implants were intended for load bearing applications, low hydration rates clearly were undesirable.

It therefore also would be desirable to provide methods of using and forming hydrogel articles that hydrate relatively quickly, and without substantial degradation of mechanical properties.

SUMMARY OF THE INVENTION

In view of the foregoing, it is an object of the present invention to provide methods of using hydrogel articles for sealing or occluding a body lumen, or tissue augmentation, that overcome the drawbacks of previously known devices and methods. It is another object of this invention to provide methods of using and forming hydrogel articles capable of undergoing a relatively large degree of swelling in-situ.

It is a further object of the present invention to provide methods of using and forming hydrogel articles for plugging voids created in tissue during surgical procedures, such as a needle track created during a biopsy, so as to reduce the risk of hemorrhage after tissue removal.

It is yet another object of this invention to provide methods of using and forming hydrogel articles that hydrate relatively quickly, and without substantial degradation of mechanical properties.

These and other objects of the invention are accomplished by providing methods of using and forming medical articles from pharmaceutically acceptable hydrogel polymer, wherein the articles are introduced in a dry, less hydrated, or substantially deswollen state, and rehydrate in a physiological environment to increase in volume. The methods of the present invention may be advantageously used to affect sealing, plugging, or augmentation of tissue, defects in tissue and organs, and may optionally permit controlled release of therapeutic agents at an implantation site. Hydrogel polymers useful for the present invention may be bioabsorbable or biostable, preferably exhibit a relatively large degree of swelling and rapid rehydration rate, and may include any of a variety of pharmaceutically acceptable or implantable hydrogel biomaterials of natural, recombinant, or of synthetic origin or hybrids thereof.

Methods to form medically useful devices in situ, and to implant devices in accordance with the principles of the present invention in a minimally invasive fashion, also are provided.

DETAILED DESCRIPTION OF THE INVENTION

In accordance with the present invention one or more rods, plugs, crushed or irregularly shaped pieces of substantially dehydrated hydrogel material are introduced into a lumen or void in a patient's body to seal or plug a biopsy needle track, serve to reinforce weak tissue, or deliver a therapeutic compound. The hydrogel polymer preferably rehydrates rapidly, within a few minutes of being placed in a moist tissue environment, so as to anchor itself within tissue. During the hydration process, the dried gel may expand volumetrically, e.g., in one, two or three dimensions, to several times its original size, thereby lodging the gel within the tissue and sealing against leakage of fluids through the tissue.

This written description comprises the following portions: a description of hydrogels suitable for use in practicing the methods of the present invention, descriptions of medical articles and methods for using the hydrogel articles of the present invention; and, example compositions of hydrogel articles and exemplary applications.

I. HYDROGEL MATERIALS SUITABLE FOR USE IN THE INVENTION

Hydrogels may be formed from covalently or non-covalently crosslinked materials, and may be non-degradable ("biostable") in a physiological environment or broken down by natural processes within the body, referred to as biodegradable or bioabsorbable. The breakdown process may be due to one of many factors in the physiological environment, such as enzymatic activity, heat, hydrolysis, or others, including a combination of these factors.

Hydrogels that are crosslinked may be crosslinked by any of a variety of linkages, which may be reversible or irreversible. Reversible linkages may be due to ionic interaction, hydrogen or dipole type interactions or the presence of covalent bonds. Covalent linkages for absorbable or degradable hydrogels may be chosen from any of a variety of linkages that are known to be unstable in an animal physiological environment due to the presence of bonds that break either by hydrolysis (e.g., as found in synthetic absorbable sutures), enzymatically degraded (e.g., as found in collagen or glycosamino glycans or carbohydrates), or those that are thermally labile (e.g., azo or peroxy linkages).

All of the hydrogel materials appropriate for use in the present invention should be physiologically acceptable and should be swollen in the presence of water. These characteristics allow the hydrogels to be introduced into the body in a "substantially deswollen" state and over a period of time hydrate to fill a void, a defect in tissue, or create a hydrogel-filled void within a tissue or organ by mechanically exerting a gentle force during expansion. The hydrogel may be pre-formed or formed in situ.

"Substantially deswollen" is defined as the state of a hydrogel wherein an increase in volume of the hydrogel of the article or device formed by such hydrogel is expected on introduction into the physiological environment. Thus, the hydrogel may be in a dry state, or less than equilibrium hydrated state, or may be partially swollen with a pharmaceutically acceptable fluid that is easily dispersed or is soluble in the physiological environment. The expansion process also may cause the implanted material to become firmly lodged within a hole, an incision, a puncture, or any defect in tissue which may be congenital, diseased, or iatrogenic in origin, occlude a tubular or hollow organ, or support or augment tissue or organs for some therapeutic purpose.

Hydrogels useful in practicing the present invention may be formed from natural, synthetic, or biosynthetic polymers. Natural polymers may include glycosaminoglycans, polysaccharides, proteins etc. The term "glycosaminoglycan" is intended to encompass complex polysaccharides which are not biologically active (i.e., not compounds such as ligands or proteins) and have repeating units of either the same saccharide subunit or two different saccharide subunits. Some examples of glycosaminoglycans include dermatan sulfate, hyaluronic acid, the chondroitin sulfates, chitin, heparin, keratan sulfate, keratosulfate, and derivatives thereof.

In general, the glycosaminoglycans are extracted from a natural source and purified and derivatized. However, they also may be synthetically produced or synthesized by modified microorganisms such as bacteria. These materials may be modified synthetically from a naturally soluble state to a partially soluble or water swellable or hydrogel state. This modification may be accomplished by various well-known techniques, such as by conjugation or replacement of ionizable or hydrogen bondable functional groups such as carboxyl and/or hydroxyl or amine groups with other more hydrophobic groups.

For example, carboxyl groups on hyaluronic acid may be esterified by alcohols to decrease the solubility of the hyaluronic acid. Such processes are used by various manufacturers of hyaluronic acid products (such as Genzyme Corp., Cambridge, Mass.) to create hyaluronic acid based sheets, fibers, and fabrics that form hydrogels. Other natural polysaccharides, such as carboxymethyl cellulose or oxidized regenerated cellulose, natural gum, agar, agrose, sodium alginate, carrageenan, fucoidan, furcellaran, laminaran, hypnea, eucheuma, gum arabic, gum ghatti, gum karaya, gum tragacanth, locust beam gum, arbinoglactan, pectin, amylopectin, gelatin, hydrophilic colloids such as carboxymethyl cellulose gum or alginate gum cross-linked with a polyol such as propylene glycol, and the like, also form hydrogels upon contact with aqueous surroundings.

Synthetic polymeric hydrogels generally swell or expand to a very high degree, usually exhibiting a 2 to 100-fold volume increase upon hydration from a substantially dry or dehydrated state. Synthetic hydrogels may be biostable or biodegradable or bioabsorbable.

Biostable hydrophilic polymeric materials that form hydrogels useful for practicing the present invention include poly(hydroxyalkyl methacrylate), poly(electrolyte complexes), poly(vinylacetate) cross-linked with hydrolysable bonds, and water-swellable N-vinyl lactams.

Other suitable hydrogels include hydrophilic hydrogels know as CARBOPOL®, a registered trademark of B.F. Goodrich Co., Akron, Ohio, for acidic carboxy polymer (Carbomer resins are high molecular weight, allylpentaerythritol-crosslinked, acrylic acid-based polymers, modified with C10-C30 alkyl acrylates), polyacrylamides marketed under the CYANAMER® name, a registered trademark of Cytec Technology Corp., Wilmington, Del., polyacrylic acid marketed under the GOOD-RITE® name, a registered trademark of B.F. Goodrich Co., Akron, Ohio, polyethylene oxide, starch graft copolymers, acrylate polymer marketed under the AQUA-KEEP® name, a registered trademark of Sumitomo Seika Chemicals Co., Japan, ester cross-linked polyglucan, and the like. Such hydrogels are described, for example, in U.S. Pat. No. 3,640,741 to Etes, U.S. Pat. No. 3,865,108 to Hartop, U.S. Pat. No. 3,992,562 to Denzinger et al., U.S. Pat. No. 4,002,173 to Manning et al., U.S. Pat. No. 4,014,335 to Arnold and U.S. Pat. No. 4,207,893 to Michaels, all of which are incorporated herein by reference, and in *Handbook of Common Polymers*, (Scott & Roff, Eds.) Chemical Rubber Company, Cleveland, Ohio.

Hydrogels also may be formed to be responsive to changes in environmental factors, such as pH, temperature, ionic strength, charge, etc., by exhibiting a corresponding change in physical size or shape, so-called "smart" gels. For example, thermoreversible hydrogels, such as those formed of amorphous N-substituted acrylamides in water, undergo reversible gelation when heated or cooled about certain temperatures (lower critical solution temperature, LCST). Prevailing gel formation mechanisms include molecular clustering of amorphous polymers and selective crystallization of mixed phases of crystalline materials. Such gels, which are insoluble under physiological conditions, also advantageously may be used for practicing the present invention.

It is also possible to affect the rate at which a substantially dehydrated hydrogel rehydrates in a physiological environment, such as encountered upon implantation in an animal. For example, creating a porous structure within the hydrogel by incorporating a blowing agent during the formation of the hydrogel may lead to more rapid re-hydration due to the enhanced surface area available for the water front to diffuse into the hydrogel structure.

When a foamed gel is desired, a two component mixture of the precursors to a hydrogel forming system may be selected such that foaming and polymerization to form the hydrogel are initiated when the two fluid channels are mixed. A double barrel syringe assembly may be provided to mix the fluids, in which each barrel is equipped with a separate plunger to force the material contained therein out through a discharge opening. The plungers preferably are connected to one another at the proximal ends so that a force exerted on the plungers generates equal pressure within each barrel and displaces both plungers an equal distance.

The hydrogel forming precursors for the foregoing system may be selected so that, for example, a free radical polymerization is initiated when two components of a redox initiating system are brought together. One of these components additionally may include a foaming agent, e.g., sodium bicarbonate, that when exposed to an acidic environment (e.g., the other component in the syringe may comprise an acidic solution), releases carbon dioxide as a foaming agent. While the effervescent compound reacts with the water-soluble acid to release gases, the hydrogel structure is polymerizing and crosslinking, thereby causing the formation of a stable foamed gel. Alternatively, other techniques, which are per se known, may be used to foam the hydrogels.

In addition, the driving force for water to penetrate a dehydrated hydrogel also may be influenced by making the hydrogel hyperosmotic relative to the surrounding physiological fluids. Incorporation of charged species within hydrogels, for example, is known to greatly enhance the swellability of hydrogels. Thus the presence of carboxyl or sulfonic acid groups along polymeric chains within the hydrogel structure may be used to enhance both degree and rate of hydration. The surface to volume ratio of the implanted hydrogels also is expected to have an impact on the rate of swelling. For example, crushed dried hydrogel beads are expected to swell faster to the equilibrium water content state than a rod shaped implant of comparable volume.

Alternatively, instead of using dehydrated preformed hydrogels, in-situ formed hydrogels formed from aqueous solutions of precursor molecules also may be used. The hydrogels may be absorbable or biostable. The precursor solutions preferably are selected so that the hydrogels when formed in the physiological environment are below the equilibrium level of hydration. Thus, when formed in-situ, the hydrogels have the ability to hydrate and increase in size. If the hydrogels are formed in confined tissue spaces, the additional swelling is expected to further anchor the hydrogel in place.

Any of a variety of techniques may be used to form hydrogels in-situ. For example, monomers or macromers of hydrogel forming compositions may be further polymerized to form three dimensionally cross-linked hydrogels. The crosslinking may be covalent, ionic, and or physical in nature. Polymerization mechanisms permitting in-situ formation of hydrogels are per se known, and include, without limitation, free radical, condensation, anionic, or cationic polymerizations. The hydrogels also may be formed by reactions between nucleophilic and electrophilic functional groups, present on one or more polymeric species, that are added either simultaneously or sequentially. The formation of hydrogels also may be facilitated using external energy sources, such as in photoactivation, thermal activation and chemical activation techniques.

Absorbable Polymeric Hydrogels

Absorbable polymers, often referred to as biodegradable polymers, have been used clinically in sutures and allied surgical augmentation devices to eliminate the need for a second surgical procedure to remove functionally equivalent non-absorbable devices. See, for example, U.S. Pat. No. 3,991,766 to Schmitt et al. and Shalaby, *Encyclopedia of Pharmaceutical Technology* (Boylan & Swarbrick, Eds.), Vol. 1, Dekker, New York, 1988, p. 465. Although these previously known devices were intended for repairing soft tissues, interest in using such transient systems, with or without biologically active components, in dental and orthopedic applications has grown significantly in the past few years. Applications of absorbable polymers are disclosed in Bhatia, et al., *J. Biomater. Sci., Polym. Ed.*, 6(5):435 (1994), U.S. Pat. No. 5,198,220 to Damani, U.S. Pat. No. 5,171,148 to Wasserman, et. al., and U.S. Pat. No. 3,991,766 to Schmitt et al.

Synthesis and biomedical and pharmaceutical applications of absorbable or biodegradable hydrogels based on covalently crosslinked networks comprising polypeptide or polyester components as the enzymatically or hydrolytically labile components, respectively, have been described by a number of researchers. See, e.g., Jarrett et al., "Bioabsorbable Hydrogel Tissue Barrier: In Situ Gelation Kinetics," *Trans. Soc. Biomater.*, Vol. XVIII, 182 (1995); Sawhney et al., "Bioerodible Hydrogels Based on Photopolymerized Poly(ethyleneglycol)-co-poly($\alpha$-hydroxy acid) Diacrylate Macromers", *Macromolecules*, 26:581-587 (1993); Park, et al., *Biodegradable Hydrogels for Drug Delivery*, Technomic Pub. Co., Lancaster, Pa. (1993); Park, "Enzyme-digestible swelling hydrogels as platforms for long-term oral delivery: synthesis and characterization," *Biomaterials*, 9:435-441 (1988). The hydrogels most often cited in the literature are those made of water-soluble polymers, such as polyvinyl pyrrolidone, which have been crosslinked with naturally derived biodegradable components such as those based on albumin.

Totally synthetic hydrogels have been studied for controlled drug release and membranes for the treatment of post-surgical adhesion. Those hydrogels are based on covalent networks formed by the addition polymerization of acrylic-terminated, water-soluble polymers that have at least one biodegradable spacer group separating the water soluble segments from the crosslinkable segments, so that the polymerized hydrogels degrade in vivo. Such hydrogels are described in U.S. Pat. No. 5,410,016, which is incorporated herein by reference, and may be particularly useful for practicing the present invention.

Preferred hydrogels for use in the present invention are formed by the polymerization of macromers that form hydrogel compositions that are absorbable in vivo. These macromers, for example, may be selected from compositions that are biodegradable, polymerizable, and substantially water soluble macromers comprising at least one water soluble region, at least one degradable region, and statistically more than 1 polymerizable region on average per macromer chain, wherein the polymerizable regions are separated from each other by at least one degradable region.

Hydrogels that have some mechanical integrity and that cannot be "extruded" from the implantation site by forces applied by natural movement of surrounding tissues are preferred for this invention. Thus, hydrogels suitable for use in the present invention preferably are physically or chemically crosslinked, so that they possess some level of mechanical integrity even when fully hydrated. The mechanical integrity of the hydrogels may be characterized by the tensile modulus at breaking for the particular hydrogel. Hydrogels having a tensile strength in excess of 10 KPa are preferred, and hydrogels having a tensile strength greater than 50 KPa are more preferred.

II. APPLICATIONS FOR IN-SITU HYDRATION

A number of applications of the foregoing hydrogels are described in accordance with the principles of the present invention. More particularly, use of hydrogel medical articles are described for numerous applications wherein the article inserted with a small profile, and upon hydration serves to occlude lumens, augment tissues or organs, or block orifices.

1. Sealing of Biopsy Tracks

Biopsy needle tracks may be embolized in accordance with the principles of the present invention to reduce complications associated with needle biopsies, such as bleeding and airleaks. A preformed plug of a hydrogel selected as described hereinabove may be placed in a needle track, for example, using the same device that was used for the tissue retrieval.

Specifically, the hydrogel plug is formed from a material exhibiting rapid hydration and swelling, and a low degree of syneresis, i.e., it does not allow absorbed fluid to be easily expelled under moderate mechanical loading. The hydrogel plug may be preformed and partially or completely dehydrated. Upon completion of a biopsy, the hydrogel plug is disposed in the needle track formed by the biopsy instrument. The plug then rehydrates and swells to become firmly lodged in the needle track. The hydrogel plug preferably is bioabsorbable, so that it may be absorbed and allow tissue to eventually fill the needle track. Alternatively, the hydrogel may be formed in-situ, as described hereinabove.

2. Bone Plugs

Bone plugs often are used to occlude the femoral canal during hip replacement surgery. Restricting the escape of uncured bone cement during the insertion of the femoral prosthesis is known to improve penetration of the cement into adjacent spongy bone and ensure complete filling of the canal, including beneath the tip of the device. Plugging the medullary canal prior to cement insertion also aids in compacting the bone cement to eliminate internal voids that may cause cracking and failure of the cement. Apart from the initial cement insertion process, this application is not a load bearing one and is thus ideally suited to the use of an absorbable hydrogel plug. After the cement has set up, within a few hours, the load is borne by the cement.

A rapidly hydrating hydrogel plug that has a "one size fits all" capability for intermedullary canals and that does not need any special tools for insertion (drop fit only), may be a convenient tool for orthopedic surgeons. It is expected that a plug of substantially dehydrated hydrogel material may be introduced into the intramedullary canal after the reaming process is complete. The plug will rehydrate within a few minutes to generate a fit sufficiently tight to prevent leakage of the bone cement. Such bone plugs are expected to have significant benefits over previously known non-degradable polyethylene plugs, which form permanent implants.

3. Suture Anchors

Hydrogel articles prepared in accordance with the principles of the present invention may be advantageously employed as bone or cartilage anchors. Suture anchors play an increasingly important role in attaching tendons or ligaments to bone, and are typically made of metallic or other nonbioabsorbable materials. Non-loadbearing indications, such as delicate maxiofacial reconstruction or repair of cartilage tears, also may benefit from a soft hydrogel-type absorbable suture anchor. The self hydrating and tightening characteristic of hydrogels may advantageously reduce problems of anchor loosening, migration, interference with imaging studies, and the potential requirement for later implant removal.

For this and the preceding applications, hydrogel material may be threaded or formed around nonabsorbable or absorbable polymer sutures to allow accurate guidance and placement of the devices. In the substantially dehydrated state the suture has a good holding or "potting" strength within the hydrogel article. Upon hydration of the hydrogel material, after the hydrogel is expected to be securely anchored at the surgical site of interest, the suture material easily may be removed. Sutures potted within the hydrogel articles may include single or composite fibers. The shape, form and diameter of the fiber may vary, and may include monofilament, multifilament, twisted thread, spun yarn, staple fiber and whisker.

4. Dental Applications

Hydrogel articles of the present invention also may be advantageously used in dentistry, for example, in occluding root canals. Generally, after a root canal has been cleaned and disinfected, the resulting passageway is occluded to prevent bacterial contamination. Often un-crosslinked rubber-type materials, such as Gutta-Percha, are used to plug these openings. Gutta-Percha, however, has no inherent form-fitting property and must be mechanically forced into the canal.

In accordance with the principles of the present invention, a rod of substantially dehydrated hydrogel material may be cut to size and introduced into the root canal, where it is allowed to hydrate, swell, and lock into place to form a tight fit. The hydrogel is expected to provide an effective barrier against oral fluids, food material, and bacteria. If a substantially non-degradable hydrogel is selected, long term occlusion may be provided. Alternatively, an absorbable material may be used if it is desirable that natural tissues replace the hydrogel over a period of time.

5. Wound Closure

Hydrogel articles of the present invention may be employed for closure of percutaneous catheter puncture sites. Most angiographic, angioplasty, and a variety of other less-invasive catheter based approaches to the vascular system are carried out by cannulating the femoral artery. Generally, a sheath is positioned through a puncture wound to provide access to the artery and allow exchange of various catheters required during a procedure. At the end of the procedure, the sheath is removed, often resulting in a considerable amount of bleeding.

In accordance with well-known techniques, manual pressure is applied to the wound for a period of about 30 to 60 minutes to prevent bleeding and allow cessation of bleeding by clot formation. Even when a clot has formed, the patient is not permitted to freely move around for fear of re-bleeding. Several medical devices, based on collagen-type materials, have been developed to fill the space or track left by the sheath. These materials are however, inherently inflammatory and pro-thrombotic, and may promote intimal hyperplasia or thrombosis of the artery. While various suturing techniques have been developed that use long needles, suture material, and knot pushing devices have been used to close the arteriotomy site, these techniques require considerable skill, especially where visualization of the site is limited.

Hydrogel articles of the present invention may be advantageously used to overcome the drawbacks of previously known wound closure systems. For example, a rod-shaped plug of a substantially desiccated hydrogel may be deployed into the site of an arteriotomy and allowed to hydrate, in the presence of the tissue fluids and blood, to rapidly fill the track of the catheter sheath and prevent further bleeding. By swelling to equilibrium hydration, the plug will lock itself firmly in place and thus reduce the risk of formation of a large hematoma at the site of the puncture.

A hydrogel rod also may be used in conjunction with a pledget configured for intraarterial placement, and that has a suture connecting it to the hydrogel rod. A pledget is a small thin resilient object, formed from polyester foam or felt, that is used to distribute a load imposed by a suture strand to surrounding tissue to prevent tearing, or to reduce bleeding at a puncture site. In this case, the pledget actually provides the arterial closure, but is anchored by the swollen hydrogel within the puncture site. The hydrogel itself may consist of a single rod or alternatively, may comprise a combination of hydrogel shapes, such as braided strands, etc. In the latter case, the resulting macroporous spaces and larger surface area are expected to permit more rapid hydration.

6. Occlusion Of Arteriovenous Malformations

Hydrogel articles of the present invention may be introduced into a patient's body in a low profile, substantially dehydrated state, such that upon hydration the hydrogel article occludes an abnormal vascular structure. Abnormal vascular connections, known as arteriovenous malformations (AVMs), may develop either as a congenital defect or as a result of iatrogenic or other trauma. An AVM may lead to a substantial diversion of blood from the intended tissue and may consequently engender a variety of symptoms, including those leading to morbidity. Subdural hematomas and bleeding also may occur as a result of the presence of an AVM.

Surgical intervention is often undertaken to correct AVMs. Interventional radiologic approaches also are used to obliterate AVMs by embolization, in which the goal of embolization is to selectively obliterate an abnormal vascular structure, while preserving blood supply to surrounding normal tissues. Embolization typically is accomplished using low-profile soft microcatheters that allow superselective catheterization into the brain to deliver an embolic material under fluoroscopic guidance. Various embolic materials have been used in endovascular treatment in the central nervous system, such as cyanoacrylates, ethylene-vinyl alcohol copolymer mixtures (EVAL), ethanol, estrogen, poly(vinyl acetate), cellulose acetate polymer, poly (vinyl alcohol) (PVA), gelatin sponges, microfibrillar collagen, surgical silk sutures, detachable balloons, and coils.

In accordance with the principles of the present invention, substantially dry hydrogel materials may be introduced with a catheter under radiographic guidance to embolize AVMs. Upon delivery to the vascular network, the hydrogel articles, which may be in rod, pellet, fiber, rolled up film or other physical form, rehydrate and occlude the vascular flow by mechanical obstruction. Preferred hydrogel materials to be used in this application should be biostable and not be degraded by the vascular environment. Where permanent embolization is desired, non-degradable hydrogel materials are preferred over degradable ones.

7. Occlusion Of Reproductive Organs

Hydrogel articles also may be introduced into the body in a low profile in a substantially dehydrated state such that, upon hydration, they occlude lumens of reproductive structures. For example, the World Health Organization has underscored the need for a rapid and minimally invasive method for female sterilization. Most sterilization techniques used currently are invasive and irreversible. Approximately 40-50% of women age 15-44 that choose to use a contraceptive method are sterilized or their husband has undergone sterilization.

Lack of reversibility and the need for a surgical procedure are major drawbacks of previously known sterilization methods. Ligation of fallopian tubes must to be conducted under epidural anesthesia and is a difficult procedure to reverse. Recently developed scarification techniques involving off-label intrauterine use of Quinacrine have been associated with morbidity and even mortality. There is, therefore a need for a safe and effective way to induce sterilization with a retained option of reversibility.

Catheters to determine the patency of fallopian tubes have been developed, for example by Conceptus Inc., San Carlos, Calif. Ultrasonic inspection for determining the patency of fallopian tubes is a well-known procedure. In accordance with one aspect of the present invention, deswollen hydrogel plug may be inserted intrauterally into the fallopian tubes. When the plugs rehydrate, they occlude the fallopian tubes and readily effect sterilization.

The use of substantially dehydrated hydrogels may permit such hydrogel plugs to be deployed in a doctor's office setting, without the need for anesthesia. If fertility is to be restored later, the hydrogel plugs may be comprise a biodegradable material that undergoes natural degradation in the physiological environment. Alternatively, the hydrogel plugs may be removed by administration of a solvating agent, or by mechanical removal, and the patency of the tubes restored and confirmed by ultrasound.

8. Sphincter Augmentation

It is estimated that at least 30 million Americans suffer from urinary incontinence. Urinary incontinence may be either temporary or permanent, and result from physiologic or neurologic deficits. Female stress incontinence, i.e., the loss of urine during everyday activities such as laughing, sneezing, coughing, etc., is the most common type of incontinence, and generally responds better to surgery than to previously known drug therapies.

Several surgical approaches have been adopted for the correction of female stress incontinence including urethral slings, bladder neck suspensions, and artificial sphincter implantation. A recent approach to sphincter augmentation uses an injectable collagen as a urethral bulking agent to correct intrinsic sphincter deficiency. Unfortunately, it has been observed that the collagen is resorbed in up to 20% of women within 9 months. Because the procedure is conducted in a minimally invasive fashion, it provides an attractive alternative to intraoperative solutions. There remains, however, a need for a more permanent way to augment the urinary sphincter with a percutaneously administered biocompatible in-situ formed bulking agent and that does not raise pose the safety risks associated with collagen.

In accordance with another aspect of the present invention, substantially dehydrated hydrogels may be percutaneously implanted into the urethral sphincter to create an elastic and tissue-like bulk that lasts several years. Any of the variety of hydrogels described hereinabove have the persistence and in vivo biocompatibility characteristics to be suitable for this process.

A similar approach also may be used to correct other sphincter deficiencies. For example, the gastro-esophageal sphincter may be percutaneously augmented to reduce gastric reflux. The pyloric sphincter also may be percutaneously augmented to reduce "dumping" problems associated with intestinal pH imbalance.

9. Medical Device Coatings

In accordance with another aspect of the present invention, a substantially dehydrated hydrogel may be used to coat a medical device, so that hydration of the coating enables the medical device to become anchored in place to prevent migration. For example, stent grafts are wire mesh type devices that are used in conjunction with a textile type woven, knit, or film type material. The wire framework mechanically hold a lumen, e.g., an artery, open, while the textile, fabric, or film provides a lumen through which fluids may flow. This approach has been successfully used in treating aneurysms, such as abdominal aortic aneurysms.

A significant shortcoming of previously known stent grafts systems, however, has been the leakage of blood around the stent graft. This bypass flow often causes the aneurysm to further increase in size, and may lead to eventual rupture.

In accordance with the principles of the present invention, a substantially dehydrated hydrogel coating is disposed on the exterior surface of the textile, fabric, or film of the stent graft. When deployed in a body lumen, the coating hydrates in the presence of blood and tightly wedges the stent graft in position. In addition, as the hydrogel hydrates it causes the stent graft to closely conform to the boundaries of the vessel, so that the blood leakage around the stent graft may be reduced.

10. Delivery of Drugs and Therapeutic Entities

Often the reason for performing a biopsy is the presence of a suspected tumor or other mass of diseased tissue. After confirmation of the biopsy identity, it may be desirable to place a therapeutic agent at the site of suspected disease. The self-anchoring swellable hydrogel articles of the present invention may enable the delivery of therapeutic entities to such sites through the same channel as the instrument that is used to perform the biopsy (or with an instrument having a similar profile).

Optionally, a hydrogel plug, such as described hereinabove, may include one or more biologically-active agents and elute the agent to adjacent or distant tissues and organs in the animal. Biologically-active agents suitable for use include, for example, medicaments, drugs, or other suitable biologically-, physiologically-, or pharmaceutically-active substances that provide local or systemic biological, physiological or therapeutic effect in the body of an animal including a mammal.

Water-soluble drugs that may be incorporated within the hydrogel articles of the present include, for example, peptides having biological activities, other antibiotics, antitumor agents, antipyretics, analgesics, anti-inflammatory agents, antitussive expectorants, sedatives, muscle relaxants, antiepileptic agents, antiulcer agents, antidepressants, antiallergic agents, cardiotonics, antiarrhythmic agents, vasodilators, hypotensive diuretics, antidiabetic agents, anticoagulants, hemostatics, antituberculous agents, hormone preparations, narcotic antagonists, bone resorption inhibitors, angiogenesis inhibitors and the like.

Examples of the foregoing antitumor agents include bleomycin hydrochloride, methotrexate, actinomycin D, mitomycin C, vinblastine sulfate, vincristine sulfate, daunorubicin hydrochloride, adriamycin, neocarzinoszatin, cytosine arabinoside, fluorouracil, tetrahydrofuryl-5-fluorouracil krestin, picibanil, lentinan, levamisole, bestatin, azimexon, glycyrrhizin, poly I:C, poly A:U, poly ICLC, cisplatin and the like.

The biologically-active agent may be soluble in the polymer solution to form a homogeneous mixture, or insoluble in the polymer solution to form a suspension or dispersion. Upon implantation, the biologically-active agent preferably becomes incorporated into the implant matrix. As the matrix degrades over time, the biologically-active agent is released from the matrix into the adjacent tissue fluids, preferably at a controlled rate. The release of the biologically-active agent from the matrix may be varied, for example, by the solubility of the biologically-active agent in an aqueous medium, the distribution of the agent within the matrix, the size, shape, porosity, solubility and biodegradability of the implant matrix, and the like.

The biologically-active agent may stimulate a biological or physiological activity with the animal. For example, the agent may act to enhance cell growth and tissue regeneration, function in birth control, cause nerve stimulation or bone growth, and the like. Examples of useful biologically-active agents include a substance, or metabolic precursor thereof, that promotes growth and survival of cells and tissues, or augments the functioning of cells, as for example, a nerve growth promoting substance such as a ganglioside, a nerve growth factor, and the like; a hard or soft tissue growth promoting agent such as fibronectin (FN), human growth hormone (HGH), protein growth factor interleukin-1(IL-1), and the like; a bone growth promoting substance such as hydroxyapatite, tricalcium phosphate, and the like; and a substance useful in preventing infection at the implant site, as for example, an antiviral agent such as vidarabine or acyclovir, an antibacterial agent such as a penicillin or tetracycline, and antiparasitic agent such as quinacrine or chloroquine.

Suitable biologically-active agents for use in the present invention also include anti-inflammatory agents such as hydrocortisone, prednisone and the like; antibacterial agents such as penicillin, cephalosporins, bacitracin and the like; antiparasitic agents such as quinacrine, chloroquine and the like; antifungal agents such as nystatin, gentamicin, and the like; antiviral agents such as acyclovir, ribavirin, interferons and the like; antineoplastic agents such as methotrexate, 5-fluorouracil, adriamycin, tumor-specific antibodies conjugated to toxins, tumor necrosis factor, and the like; analgesic agents such as salicylic acid, acetaminophen, ibuprofen, flurbiprofen, morphine and the like; local anesthetics such as lidocaine, bupivacaine, benzocaine and the like; vaccines such as hepatitis, influenza, measles, rubella, tetanus, polio, rabies and the like; central nervous system agents such as a tranquilizer, B-adrenergic blocking agent, dopamine and the like; growth factors such as colony stimulating factor, platelet-derived growth factors, fibroblast growth factor, transforming growth factor B, human growth hormone, bone morphogenetic protein, insulin-like growth factor and the like; hormones such as progesterone, follicle stimulating hormone, insulin, somatotropins and the like; antihistamines such as diphenhydramine, chlorphencramine and the like; cardiovascular agents such as digitalis, nitroglycerine, papaverine, streptokinase and the like; vasodilators such as theophylline, niacin, minoxidil, and the like; and other like substances.

Therapeutic agents that may be delivered may include for example, physiologically active materials or medicinal drugs (such as agents affecting central nervous system, antiallergic agents, cardiovascular agents, agents affecting respiratory organs, agents affecting digestive organs, hormone preparations, agents affecting metabolism, antitumor agents, antibiotic preparations, chemotherapeutics, antimicrobials, local anesthetics, antihistaminics, antiphlogistics, astringents, vitamins, antifungal agents, peripheral nervous anesthetics, vasodilators, crude drug essences, tinctures, crude drug powders, hypotensive agents, and the like).

The terms "cytokine" and "growth factor" are used to describe biologically active molecules and active peptides (which may be either naturally occurring or synthetic) that aid in healing or regrowth of normal tissue, including growth factors and active peptides. The function of cytokines is two-fold: 1) to incite local cells to produce new collagen or tissue, or 2) to attract cells to the site in need of correction. As such, cytokines and growth factors serve to encourage "biological anchoring" of the implant within the host tissue. As previously described, the cytokines may be admixed with the conjugate or chemically coupled to the conjugate.

For example, one may incorporate cytokines such as interferons (IFN), tumor necrosis factors (TNF), interleukins, colony stimulating factors (CSFs), or growth factors such as osteogenic factor extract (OFE), epidermal growth factor (EGF), transforming growth factor (TGF) alpha, TGF-β_ (including any combination of TGF-βs), TGF-β1, TGF-β2, platelet derived growth factor (PDGF-AA, PDGF-AB, PDGF-BB), acidic fibroblast growth factor (FGF), basic FGF, connective tissue activating peptides (CTAP), β-thromboglobulin, insulin-like growth factors, erythropoietin (EPO), nerve growth factor (NGF), bone morphogenic protein (BMP), osteogenic factors, and the like.

The hydrogels of the present invention also may provide controlled delivery of various antibiotics, including, for example, aminoglycosides, macrolides such as erythromycin, penicillins, cephalosporins and the like; anesthetic/analgesic delivery pre- or post surgery or to treat pain using such agents as amide-type local anesthetics like lidocaine, mepivacaine, pyrrocaine, bupivacaine, prilocaine, etidocaine, or the like; and local controlled delivery of non-steroidal anti-inflammatory drugs such as ketorolac, naproxen, diclofenac sodium and flurbiprofen.

In certain forms of therapy, the same delivery system, i.e., hydrogel article, may be used to deliver combinations of agents/drugs to obtain an optimal effect. Thus, for example, an antibacterial and an anti-inflammatory agent may be combined in a single polymer to provide combined effectiveness.

Particular water-soluble polypeptides that may be used in the hydrogel articles of the present invention include, for example, oxytocin, vasopressin, adrenocorticotrophic hormone (ACTH), epidermal growth factor (EGF), transforming growth factor antagonists, prolactin, luliberin or luteinizing hormone releasing hormone (LH-RH), LH-RH agonists or antagonists, growth hormone, growth hormone releasing factor, insulin, somatostatin, bombesin antagonists, glucagon, interferon, gastrin, tetragastrin, pentagastrin, urogastrone, secretin, calcitonin, enkephalins, endomorphins, angiotensins, renin, bradykinin, bacitracins, polymyzins, colistins, tyrocidin, gramicidines, and synthetic analogues and modifications and pharmaceutically-active fragments thereof, monoclonal antibodies and soluble vaccines.

Other beneficial drugs are known in the art, as described in *Pharmaceutical Sciences*, by Remington, 14th Ed., Mack Publishing Co. (1979); *The Drug, The Nurse, The Patient, Including Current Drug Handbook*, by Falconer et al., Saunder Company (1974-76); and *Medicinal Chemistry*, 3rd Ed., Vol. 1 and 2, by Burger, Wiley-Interscience Co.

The hydrogel polymers of the present invention may be designed to release appropriate encapsulated, or uncapsulated, growth factors, including epidermal growth factors, human platelet derived TGF-B, endothelial cell growth factors, thymocytic-activating factors, platelet derived growth factors, fibroblast growth factor, fibronectin or laminin.

Useful release rate modification agents may be dissolved or dispersed within the hydrogel material, and include, for example, organic substances that are water-soluble, water-miscible, or water-insoluble (i.e., water immiscible), with water-insoluble substances preferred. The release rate modification agent preferably is an organic compound that substitutes as the complementary molecule for secondary valence bonding between polymer molecules, and increases the flexibility and ability of the polymer molecules to slide past each other. Such an organic compound preferably includes a hydrophobic and a hydrophilic region so as to effect secondary valence bonding. Preferably, the release rate modification agent is compatible with the combination of polymers and solvent used to formulate polymer solution. It is further preferred that the release rate modification agent be a pharmaceutically-acceptable substance.

Useful release rate modification agents include, for example, fatty acids, triglycerides, other like hydrophobic compounds, organic solvents, plasticizing compounds and hydrophilic compounds. Suitable release rate modification agents include, for example, esters of mono-, di-, and tricarboxylic acids, such as 2-ethoxyethyl acetate, methyl acetate, ethyl acetate, diethyl phthalate, dimethyl phthalate, dibutyl phthalate, dimethyl adipate, dimethyl succinate, dimethyl oxalate, dimethyl citrate, triethyl citrate, acetyl tributyl citrate, acetyl triethyl citrate, glycerol triacetate, di(n-butyl)sebecate, and the like; polyhydroxy alcohols, such as propylene glycol, polyethylene glycol, glycerin, sorbitol, and the like; fatty acids; triesters of glycerol, such as triglycerides, epoxidized soybean oil, and other epoxidized vegetable oils; sterols, such as cholesterol; alcohols, such as $C_6$-$C_{12}$ alkanols, 2-ethoxyethanol, and the like.

The release rate modification agent may be used singly or in combination with other such agents. Suitable combinations of release rate modification agents include, for example, glycerin/propylene glycol, sorbitol/glycerine, ethylene oxide/propylene oxide, butylene glycol/adipic acid, and the like. Preferred release rate modification agents include dimethyl citrate, triethyl citrate, ethyl heptanoate, glycerin, and hexanediol.

III. EXAMPLES

Example 1

Formation of Deswollen Hydrogel Rods

Hydrogels may be made using a poly(ethylene glycol) diacrylate macromonomer (M.W. 20,000) at a concentration of 10%. 3 μl/ml of a photoinitiator solution, such as Irgacure 651, available from Ciba Specialty Chemicals Corp., Switzerland, dissolved in N-vinyl pyrrolidinone at a concentration of 0.6 g/ml) is added to the macromer solution. The solution may be injected into hollow glass tubes with an inner diameter of 4 mm and illuminated with ultraviolet light from a Blak Ray B-100A lamp for 1 min. The polymerized rods are then extruded from the glass tubes and allowed to dry in an oven at 60° C. for 24 hrs. At the end of this period the rods should have substantially shrunk in overall size. When placed in an aqueous environment (such as physiological saline) the rods should hydrate within 15-30 minutes to several times the dried size.

Example 2

Use of Hydrogel Rods to Seal Parenchymal Lung Tissue

A freshly explanted pig lung is cored to retrieve a biopsy of lung parenchymal tissue using a side cutting biopsy needle (Cook Incorporated, Bloomington, Ind.). On inflation of the lung with an ambulatory bag an airleak should be evident at the site of the needle biopsy. A rod-shaped hydrogel article prepared according to Example 1 is placed within the site of the needle puncture. The natural tissue fluids and moisture present in the needle puncture will cause the dried hydrogel to rehydrate over a few minutes to effectively plug the airleak. On subsequent inflation, no airleak should be evident and the rod of hydrogel should be firmly lodged within the needle track.

Example 3

Enhancement of Rate of Hydration

It is possible to enhance the swelling rate by making the dried hydrogel hypertonic by the addition of water soluble salts or other agents, including solvents or low molecular weight excipients or oligomers. Such agents rapidly dissolve in an aqueous setting and generate an osmotic driving force that accelerates the hydration process.

Example 4

Further Enhancement of Rate of Hydration

Macro- or microporosity or surface texture may be created in the hydrogels to increase the surface area for ingress of aqueous fluids, thereby enhancing hydration or control of hydration. Pores formed in the dried hydrogel may create capillary forces that, i.e., a sponge-like effect, to cause rapid absorption of water and concomitant rapid expansion and deployment of the hydrogel.

Example 5

Further Enhancement of Rate of Hydration

The molecular weight between crosslinks may be used as a measure to control the rate of hydration. Thus, hydrogels may be prepared as described in Example 1 with PEG diacrylate macromers of varying molecular weights. The lower molecular weight macromers should yield a more rapid hydration, while the higher molecular weigh macromers should yield a slower hydration. This result obtains because the longer segments in between crosslinks that take longer to unravel completely. This phenomena also may lead to a greater total hydration for the higher molecular weight hydrogels compared to the lower molecular weight hydrogels.

Example 6

Use of Natural Hydrogel Materials

A sheet of a hydrogel forming natural material, such as SEPRAFILM™, marketed by Genzyme Corporation, Cambridge, Mass., is trimmed to form a piece approximately 2 cm square. The piece is rolled from one edge to the other to form a "carpet roll". The roll then may be inserted into a needle biopsy track, as described in Example 2. Hydration of the sheet over a few minutes is expected to resulted in an effective sealing of the site of airleak. Since the SEPRAFILM™ material is known to be bioabsorbed over a few weeks, it is expected that, in vivo, the lung tissues will heal around this material as it undergoes bioabsorption, thus forming a permanent seal even after absorption of the material.

Example 7

Use of a Suture Embedded Within the Hydrogel

A hydrogel rod is formed as described in Example 1, except that suture material (e.g., 3-O VICRYL®, available from Ethicon, Inc., New Brunswick, N.J.) is placed within the macromer solution in a hollow glass tube that has an inner diameter of 1.5 cm. The suture may be placed within the macromer solution prior to polymerization, so that the hydrogel formed by polymerization contains the distal end of the suture embedded in it, while the proximal end of the suture is free for manipulation. When dried, the suture should be firmly embedded within the hydrogel rod, enabling the rod of hydrogel to be easily manipulated using the suture.

Example 8

Use of a Suture Embedded Hydrogel as a Bone Plug

A rod of dried hydrogel that contains an embedded suture is prepared as described in Example 7. A lamb femur bone is obtained from an abattoir. The distal 5 cm of the bone may be sawed off to expose the intramedullary canal. The intramedullary canal is drilled to simulate a procedure wherein a hip stem is implanted and fixed with a bone cement. The rod of dried hydrogel may be maneuvered 3 cm deep within the intramedullary canal until satisfactory placement depth is obtained by measuring the suture length remaining outside the femur.

Saline solution then is instilled within the intramedullary canal and the hydrogel allowed to hydrate until it is found to have formed an adequate friction fit within the bone. At this stage the suture may be easily retrieved, because its holding strength within the hydrated gel should be lower than that in the dried hydrogel. Subsequent instillation of bone cement within the cavity may be used to verify that an effective plugging of the intramedullary canal has been achieved.

Example 9

Use of a Hydrogel as a Cervical Canal Plug

A hydrogel plug selected in accordance with the principles of the present invention advantageously may be used to plug a cervical canal following a tear in the amniotic membrane, which otherwise might lead to a forced pre-term birth. A plug about 3-4 mm in diameter is used to block the cervical opening to prevent fluid drainage or leakage. The plug should fall out when the cervix dilates naturally for normal birth and then may be easily removed.

Example 10

Use of a Hydrogel Coating on Sutures

A braided suture material (5-O Vicryl, available from Ethicon Inc., New Brunswick, N.J.) is dipped in the photopolymerizable macromer solution described in Example 1. Excess macromer solution may be removed until a thin coating about 50-100 μm remains. The suture then is exposed to long wave ultraviolet light to polymerize the hydrogel around the suture material. The suture is allowed to dry in an oven at 50° C. overnight.

An arterial anastomosis of a porcine carotid artery may be performed using either the coated suture or, as a control, uncoated suture material. The arteries are perfused with saline at a pressure of 120 mm Hg for 15 minutes with saline that contains a dye (methylene blue, 0.2 mg/ml). Initially, both anastamoses should be found to ooze through the suture line needle holes. This is expected, because the needle typically has a larger diameter than the suture, resulting in a hole that is larger in size than the suture left behind in the tissue. Within 5 minutes, the coated suture line should have sealed the needle holes due to the hydration of the coating, while the control suture line should continue to ooze.

Example 11

Use of a Hydrogel Plug for Occlusive Sterilization

Occlusion of lumens of the reproductive systems may be effected to accomplish male/female sterilization. For instance, the fallopian tubes of a woman may be occluded to obstruct the path of the egg, while in men the vas deferens may be occluded to interrupt the passage of sperm through the spermatic duct. Such occlusion of lumens may be accomplished using rods of dried up hydrogels that are placed within the lumen and are allowed to rehydrate in the presence of moisture (in the body), increase in volume, and gradually occlude the lumen. In order to prevent migration of the hydrogel plugs, the diameters of the hydrogel plugs at equilibrium hydration may be selected to be larger than the lumen to be occluded. The hydrogel rods also may include a radio-opaque contrast agent to assist in placing the plugs. Further, the hydrogel plugs may be formed from absorbable hydrogels, to provide reversible sterilization. Alternatively, alginate-based gels that have been crosslinked with calcium may be used to form hydrogel plugs. Such plugs may be reinforced with an interior mesh or matrix and include a short anchoring suture. The hydrogel plugs may be dried (or freeze dried to allow rapid rehydration), and would swell upon placement within the lumen to occlude the lumen. For reversal of sterilization, a solution of citric acid may be administered intrauterially to redissolve the plugs and restore patency, as confirmed, for example, by dye instillation.

Example 12

Use of a Hydrogel Plug to Close a Bronchial Fistula

A hydrogel rod is formed as described in Example 8, except that the rod is formed in a mold 5 mm in diameter and has a 50 cm long suture embedded in it. The hydrogel is dried to a diameter of about 1.5 mm. The hydrogel may be placed in a catheter comprising a hollow flexible tube with a distal opening and a proximal end that remains outside the patient. The distal end may be maneuvered through the operating channel of a bronchoscope and into the bronchial tree to implant the hydrogel rod.

In an explanted porcine lung, a fistula may be created by incising a segmental bronchus in the left lower lobe. Airleaks should be apparent when the lung is forcibly ventilated with an ambulatory bag. Using a 3 mm flexible bronchoscope, the segmental bronchus is visualized and the hydrogel is ejected from the distal end of the catheter using a pusher or a guidewire. The suture attached to the hydrogel rod is used in conjunction with the guidewire to achieve accurate placement. Secretions present within the bronchial tree should enable the hydrogel to hydrate and expand. After a 10 minute period, the hydrogel should be firmly lodged within the bronchiole. The suture may now be detached and the bronchoscope withdrawn. When ventilation is resumed, after about 15 minutes, the bronchus should be effectively occluded and no airleak should be evident.

Example 13

Use of Hydrogel to Seal Cerebrospinal Fluid Leaks

Surgical treatment of tumors near the skull base generally entail a transsphenoidal approach, wherein surgery is performed through a nasal cavity. A common complication of this type of surgical procedure is a cerebrospinal fluid leak due to rupture of the sellar floor. Persistent rhinorrhea may result, which is considered a major complication of surgery and may lead to life-threatening infections. Typically, at the end of such surgeries abdominal fat is harvested and used to plug the nasal cavity. There is therefore a need for a synthetic material that could be used for this purpose to obviate the surgical procedure to harvest the fat and reduce morbidity to the patient.

In accordance with the principles of the present invention, a hydrogel plug prepared as described in Example 6 may be introduced transnasally and allowed to hydrate and effectively plug the nasal cavity, thus preventing leakage of cerebrospinal fluid.

Example 14

Increased Rate of Hydration by Micropores

The process of freeze drying or lyophilization creates macro and micropores within a dried hydrogel. These pores allow more rapid ingress of water and other aqueous fluids into the hydrogel, and cause the dry hydrogel to hydrate at a rate faster than that of an oven-dried hydrogel. The phenomenon may be illustrated by making two identical hydrogels as described in Example 1. The first hydrogel is allowed to dry in an oven at 50° C. overnight; the other hydrogel is frozen at −40° C. and then allowed to gradually freeze dry over a period of 1 day. The hydrogels obtained then are allowed to rehydrate in physiological saline. The normalized weights of the two hydrogels may be compared as wet weight/dry weight over a period of time. It is expected that the macroporous lyophilized dry hydrogel hydrates at a substantially faster rate than the oven-dried hydrogel.

Example 15

Use of Osmolality Enhancing Agents to Speed Hydration

The driving force of aqueous fluid ingress in a hydrogel is primarily the osmotic potential difference between the collapsed dried or non-equilibrium hydrated hydrogel. Thus, the rate of fluid uptake of hydration may be enhanced by incorporating osmolality enhancing agents in the hydrogel.

A macromer solution is formulated as described in Example 1 and divided into two aliquots. In the first aliquot 200 mg/ml of NaCl is added; nothing is added further to the other aliquot. Rod shaped hydrogels are prepared from both formulations as described in Example 1. The hydrogel rods then are allowed to further hydrate by placing them in a physiological salt solution, without first drying the rods. It is expected that the hydrogel containing the NaCl will hydrate at a significantly faster rate to its equilibrium level than the control hydrogel.

Example 16

Use of a Wetting Agent or Consolute to Speed Hydration

In the experiment of Example 14, hydration of the lyophilized dry hydrogel is expected to be somewhat impeded by the presence of air bubbles present in the macro and micropores. PEG 600 may be added to the macromer solution described in Example 1 at a concentration of 5 mg/ml and a hydrogel further formed and lyophilized as described in Example 14. The lyophilized rod of dry hydrogel is expected to be more pliable. When the hydrogel rod is rehydrated in normal saline, it is expected that the hydrogel including the PEG 600 as a wetting agent will rehydrate somewhat faster than the rod of lyophilized hydrogel that did not have any wetting agent incorporated.

Also, during the rehydration, it is expected that few air bubbles will be observed in the hydrogel that contains the wetting agent. The mechanism for this increased rate of hydration is not readily apparent and may be due to the improved wetting characteristics of the hydrogel, the more expanded structure of the hydrogel in the water depleted form, or reduced interfacial tension between the water and the air present within the micropores, thus allowing easy access to the interior structure of the hydrogel. That the mechanism is unknown, however, does not reflect on the utility of, or otherwise limit, the invention.

Modifications and variations of the present invention, the macromers and polymeric compositions and methods of use thereof, will be apparent to those skilled in the art from the foregoing detailed description. While preferred illustrative embodiments of the invention are described above, it will be apparent to one skilled in the art that various changes and modifications may be made therein without departing from the invention and it is intended in the appended claims to cover all such changes and modifications which fall within the true spirit and scope of the invention.

The invention claimed is:

1. A method of preventing bleeding via a percutaneous puncture site comprising:
    providing a hydrogel article in a substantially deswollen state preformed as a rolled sheet;
    deploying the hydrogel article into the percutaneous puncture site; and
    allowing the hydrogel article to hydrate and expand within the puncture site to prevent bleeding via the percutaneous puncture site.

2. The method of claim 1, wherein the hydrogel article is formed from a freeze dried hydrogel.

3. The method of claim 1, wherein the expansion of the hydrogel article anchors the hydrogel article within the percutaneous puncture site.

4. The method of claim 1, wherein the hydrogel article is bioabsorbable.

5. The method of claim 1, wherein the hydrogel article is delivered to the puncture site via a sheath.

6. The method of claim 1, wherein the hydrogel article is formed as a porous structure so as to accelerate the rate of expansion of the hydrogel article within the puncture site.

7. The method of claim 1, wherein the hydrogel article comprises a sterilized pharmaceutically acceptable covalently crosslinked hydrogel polymerized from at least one synthetic hydrophilic polyethylene glycol macromer.

8. The method of claim 1, wherein the hydrogel article has an outer diameter of no more than 1.5 mm.

9. The method of claim 1, wherein the hydrogel article is biodegradable.

10. A method for closure of a percutaneous puncture site, comprising:
    positioning a sheath through a puncture wound to provide access to an artery;
    removing the sheath from the puncture wound after completing a procedure;
    introducing a bioabsorbable, freeze dried hydrogel comprising a preformed rolled sheet into the puncture wound via a tubular device;
    exposing the hydrogel to fluids within the puncture wound, the hydrogel hydrating and expanding within the puncture wound to seal the puncture wound.

11. The method of claim 10, wherein the hydrogel comprises pores formed during the freeze drying process.

12. The method of claim 10, wherein the puncture wound communicates with a femoral artery.

13. The method of claim 10, wherein the hydrogel article comprises a sterilized pharmaceutically acceptable covalently crosslinked hydrogel polymerized from at least one synthetic hydrophilic polyethylene glycol macromer.

14. The method of claim 10, wherein the hydrogel is biodegradable.

* * * * *